United States Patent [19]
Ganguly et al.

[11] 4,006,225
[45] Feb. 1, 1977

[54] METHOD OF USING REDUCTION PRODUCTS OF EVERNINOMICINS AS ANTIBACTERIAL AGENTS AND PHARMACEUTICAL COMPOSITIONS USEFUL THEREFOR

[75] Inventors: Ashit K. Ganguly, Upper Montclair; Olga Sarre, Verona, both of N.J.

[73] Assignee: Schering Corporation, Kenilworth, N.J.

[22] Filed: Apr. 21, 1975

[21] Appl. No.: 570,117

Related U.S. Application Data

[60] Division of Ser. No. 411,548, Oct. 31, 1973, Pat. No. 3,915,956, which is a continuation-in-part of Ser. No. 377,344, July 9, 1973, abandoned, which is a continuation-in-part of Ser. No. 315,263, Dec. 14, 1972, abandoned.

[52] U.S. Cl. ................................. 424/180; 536/17
[51] Int. Cl.$^2$ ........................................ A61K 31/70
[58] Field of Search ........................... 424/180, 117

[56] References Cited

UNITED STATES PATENTS 3,499,078   3/1970   Luedemann et al. ............. 424/117

*Primary Examiner*—Lewis Gotts
*Assistant Examiner*—Cary Owens
*Attorney, Agent, or Firm*—Mary S. King

[57] ABSTRACT

Everninomicin antibiotics having a nitro function, e.g. everninomicin B, everninomicin C, and everninomicin D, upon treatment with aluminum amalgam in aqueous alkanol are converted to a mixture of at least two reduction products having antibacterial activity, said reduction products being an everninomicin having a nitroso function and an everninomicin having a hydroxylamino function. The nitrosoeverninomicins are also prepared by treating the corresponding hydroxylaminoeverninomicin with an oxidizing reagent selected from the group consisting of aerial oxidation in alkaline solution, and an alkali metal hypobromite in an aprotic solvent. The everninomicin reduction products and salts thereof are described as well as nitrone derivatives of the hydroxylaminoeverninomicins and salts thereof, all of which possess antibacterial activity. A preferred compound is hydroxylaminoeverninomicin D, particularly the sodium salt thereof.

6 Claims, No Drawings

METHOD OF USING REDUCTION PRODUCTS OF EVERNINOMICINS AS ANTIBACTERIAL AGENTS AND PHARMACEUTICAL COMPOSITIONS USEFUL THEREFOR

CROSS REFERENCE TO RELATED APPLICATIONS

This application is a division of co-pending application U.S. Ser. No. 411,548, filed Oct. 31, 1973, now U.S. Pat. No. 3,915,956 in turn a continuation-in-part of application U.S. Ser. No. 377,344, filed July 9, 1973, now abandoned, in turn a continuation-in-part of application U.S. Ser. No. 315,263, filed Dec. 14, 1972, now abandoned.

FIELD OF INVENTION

This invention relates to novel compositions of matter and to processes for their preparation.

More specifically, this invention relates to everninomicins having a nitroso or a hydroxylamino function and derivatives thereof which exhibit antibacterial properties, and to methods for their preparation.

In particular, this invention relates to antibacterials selected from the group consisting of nitrosoeverninomicin B, nitrosoeverninomicin C, nitrosoeverninomicin D, hydroxylaminoeverninomicin B, hydroxylaminoeverninomicin C, hydroxylaminoeverninomicin D, nitrone derivatives of said hydroxylaminoeverninomicins, and pharmaceutically acceptable salts of the foregoing. This invention also relates to the processes for preparing the foregoing antibacterials and derivatives thereof and to intermediates produced thereby.

Prior Art

A mixture of everninomicin antibiotics, including everninomicin B, everninomicin C, and everninomicin D are produced when *Micromonospora carbonacea var. carbonacea* and a variant thereof, *Micromonospora carbonacea var. aurantiacea* are subjected to submerged aerobic fermentation under conditions described in U.S. Pat. No. 3,499,078.

Described in the art are the physical characteristics of everninomicin B and everninomicin D, each of which contain a nitro function. We have now determined that everninomicin C also contains a nitro function.

By our invention we have discovered that when an everninomicin antibiotic having a nitro function, e.g. everninomicin B, everninomicin C, and everninomicin D, is treated with aluminum amalgam in an aqueous alkanol, there is produced a mixture of at least two reduction products having antibacterial activity, said reduction products being the corresponding everninomicin wherein said nitro group has been converted to a nitroso or a hydroxylamino function, e.g. nitrosoeverninomicin B and hydroxylaminoeverninomicin B, nitrosoeverninomicin C and hydroxylaminoeverninomicin C, and nitrosoeverninomicin D and hydroxylaminoeverninomicin D, respectively.

It is apparent that each of the aforementioned hydroxylaminoeverninomicin antibacterials can also be prepared by reducing the corresponding nitrosoeverninomicins by methods known to reduce nitroso functions to hydroxylamino functions.

By our invention, we have also discovered that the nitrosoeverninomicin antibacterials are preferably prepared by oxidizing the corresponding hydroxylaminoeverninomicin antibacterial by means selected from the group consiting of aerial oxidation in alkaline solution, and an alkali metal hypobromite in an aprotic solvent.

We have further determined the structure of everninomicin B, everninomicin C, and everninomicin D and reduction products thereof as disclosed hereinbelow.

SUMMARY OF INVENTION

In one process of the invention sought to be patented, an everninomicin antibiotic having a nitro group is treated with aluminum amalgam whereby is produced a mixture of antibacterials comprising at least two everninomicin reduction products having antibacterial activity, said mixture comprising a member selected from the group consisting of a nitrosoeverninomicin and a hydroxylaminoeverninomicin. When the nitro-containing everninomicin antibiotic starting compound of this process is a member selected from the group consisting of everninomicin B, everninomicin C, and everninomicin D, there is produced an antibacterial mixture comprising a member selected from the group consisting of nitrosoeverninomicin B and hydroxylaminoeverninomicin B, nitrosoeverninomicin C and hydroxylaminoeverninomicin C, and nitrosoeverninomicin D and hydroxylaminoeverninomicin D, respectively. A preferred species of this process is that wherein everninomicin D is the starting antibiotic, wherein said aluminum amalgam is an amalgam of Reynolds Wrap aluminum foil, and wherein said process is carried out in aqueous lower alkanol, whereby is produced a mixture of antibiotics comprising a member selected from the group consisting of nitrosoeverninomicin D and hydroxylaminoeverninomicin D.

In another process aspect of this invention, a hydroxylaminoeverninomicin antibacterial is treated with an oxidizing reagent selected from the group consisting of aerial oxidation in an alkaline solution, and an alkali metal hypobromite in an aprotic solvent whereby is produced a nitrosoeverninomicin having antibacterial activity. When the starting compound of this process is a member selected from the group consisting of hydroxylaminoeverninomicin B, hydroxylaminoeverninomicin C and hydroxylaminoeverninomicin D, there is produced a nitrosoeverninomicin selected from the group consisting of nitrosoeverninomicin B, nitrosoeverninomicin C, and nitrosoeverninomicin D.

In its composition of matter aspect, the invention sought to be patented resides in the concept of an everninomicin derivative selected from the group consisting of nitrosoeverninomicin B, nitrosoeverninomicin C, nitrosoeverninomicin D, hydroxylaminoeverninomicin B, hydroxylaminoeverninomicin C, hydroxylaminoeverninomicin D, nitrone derivatives of the foregoing hydroxylaminoeverninomicins, and pharmaceutically acceptable salts of the foregoing. A preferred species of this aspect of our invention is hydroxylaminoeverninomicin D and nitrone derivatives thereof and the pharmaceutically acceptable salts of the foregoing which are more rapidly absorbed than, and have antibacterial activity comparable to that of everninomicin D. Of particular value as an antibacterial is hydroxylaminoeverninomicin D sodium salt.

GENERAL DESCRIPTION OF THE INVENTION

The Reduction Process

Our process whereby an everninomicin antibiotic having a nitro group is treated with aluminum amalgam to produce a mixture comprising at least two antibacterials selected from the group consisting of a nitrosoeverninomicin and a hydroxylaminoeverninomicin, is usually carried out at room temperature in an aqueous alkanol (preferably aqueous ethanol).

The aluminum amalgam for use in our process is prepared from aluminum and mercuric chloride in alkali according to known procedures. We have found that our process proceeds at a faster rate and produces higher yields of hydroxylaminoeverninomicin when the aluminum amalgam is freshly prepared just prior to use in our reduction process and when the amalgam is prepared with aluminum foil which is comprised essentially of from about 98% to about 99.5% aluminum usually together with trace quantities of at least one member selected from the group consisting of copper, silicone and iron, particularly when prepared with the aluminum foil sold commercially under the trade name *Reynold's Wrap* which usually comprises from about at least 99.35% aluminum and about 0.12% copper. When preparing the amalgam, we usually cut the aluminum foil in 0.5 cm. squares which are then folded at random into ball-like shapes prior to treatment with alkali and mercuric chloride.

The starting compounds for our process are everninomicin antibiotics having a nitro group, particularly everninomicin B, everninomicin C, and everninomicin D which are known antibiotics produced by the aerobic fermentation of *Micromonospora carbonacea var. carbonacea* and a variant thereof *Micromonospora carbonacea var. aurantia* according to procedures known in the art such as described in U.S. Pat. No. 3,499,078. The isolation and purification of everninomicins B and D are carried out essentially as described in the art and the isolation, purification and characterization of everninomicin C are carried out in a similar manner as described herein.

Of antibiotics everninomicins B, C, and D, everninomicin D is most readily available and is a preferred starting compound for our reduction process since there is produced therefrom good yields of hydroxylaminoeverninomicin D, a preferred compound of the composition of matter aspect of our invention. Everninomicin D is a compound of following structural formula I wherein X is nitro, i.e. X is

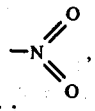

, Y is hydrogen, and Z is

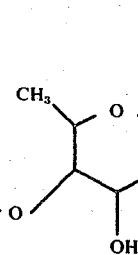

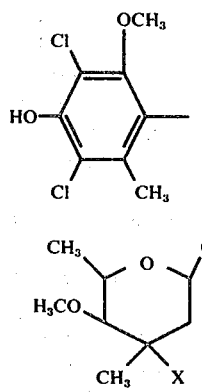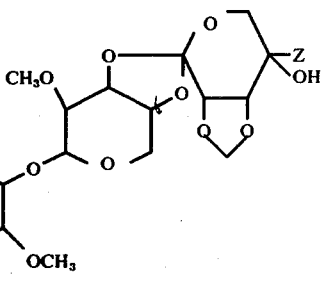

By our reduction process, the nitro group in the evernitrose sugar group present in everninomicin D, as defined by above structural formula 1, is reduced to produce a mixture of products comprising at least two novel compounds having antibacterial activity; in one, the nitro group has been reduced to a nitroso function (i.e. to a compound of formula I wherein Y is hydrogen, X is —N=O and Z is

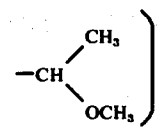

to produce nitrosoeverninomicin D; in another, the nitro group has been reduced to a hydroxylamino function (i.e. to a compound of structural formula I wherein X is

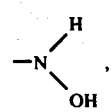

,

Y is hydrogen and Z is

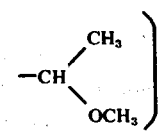

to produce hydroxylaminoeverninomicin D.

Other starting intermediates of our process, i.e. everninomicin B and C, also possess the evernitrose sugar group, the nitro function of which is reduced upon treatment with aluminum amalgam in aqueous alkanol to produce a mixture of antibacterials comprising at least two having a structure corresponding to that of the starting everninomicin, but with the nitro group of the everninomicin starting compound replaced by a nitroso or hydroxylamino function. The everninomicin B derivatives are compounds of formula I wherein Y is hydroxyl and Z is

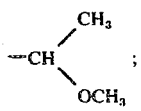

;
whereas everninomicin C derivatives are compounds of formula I wherein Y is hydrogen and Z is hydrogen.

When carrying out our reduction process, it is advantageous to repurify the starting everninomicin antibiotic just prior to treatment thereof with aluminum amalgam in aqueous ethanol, since greater yields of the corresponding hydroxylaminoeverninomicin are produced thereby. Thus, for example, when utilizing everninomicin D as starting antibiotic, it is usually purified just prior to reduction with aluminum amalgam so as to obtain everninomicin D having the following physical constants:
$R_f$ of 0.79 in a 60%-acetone-40% benzene system;
Specific Optical Rotation: $[\alpha]_D^{26}$ −34.2° (chloroform);
Neutralization Equivalent: 1563 (Calculated neutralization equivalent for $C_{66}H_{99}O_{35}NCl_2$=1537)
pKa: 7.2;

| | | Percent Found | Percent Calculated for $C_{66}H_{99}O_{35}NCl_2$ |
|---|---|---|---|
| Combustion Analysis: | Carbon | 51.64 | 51.56 |
| | Hydrogen | 6.57 | 6.49 |
| | Nitrogen | 0.83 | 0.91 |
| | Chlorine | 4.38 | 4.61 |

This is conveniently accomplished by reprecipitating everninomicin D at least twice in acetone/petroleum ether/ethyl ether followed by further purification of the reprecipitated everninomicin D by column chromatography using silica gel, eluting with acetone-benzene solvent mixtures, then combining the purest fractions as determined by thin layer chromatography. The purified everninomicin D is preferably stored underneath an atmosphere of nitrogen at about 5° C to minimize undesirable side reactions such as hydrolysis and oxidation reactions.

We have found that a 50:50 alcohol:water mixture is advantageously employed in our process, however, other alcohol: water ratios may be used. In general, the amount of water in alcohol is limited by the solubility of the starting antibiotic, the reaction rate of our process being considerably slower when the starting everninomicin is insoluble in the solvent mixture. We have found that everninomicin D remains essentially unchanged when treated via conventional reducing means, e.g., by hydrogenation in the presence of a catalyst such as palladium, Raney Nickel, palladium on charcoal, platinum, and the like. It is thus surprising that by our process an everninomicin containing a nitro group, e.g. everninomicin B, C, or D, is reduced by means of aluminum foil amalgam in aqueous alkanol to produce a product mixture comprising the corresponding nitrosoeverninomicin and hydroxylaminoeverninomicin.

Our reduction process is usually carried out under an inert atmosphere (e.g. under an atmosphere of argon or preferably nitrogen), although it may be carried out in the presence of air.

A convenient method of carrying out our reduction process comprises preparing a solution of purified everninomicin in an approximately 50:50 aqueous ethanol solvent mixture and adding aluminum amalgam freshly prepared from Reynolds Wrap aluminum foil, the amount of amalgam employed per gram of everninomicin starting compound usually being that prepared from up to two grams of aluminum (i.e. the weight of aluminum being up to twice that of starting antibiotic). The foregoing mixture is stirred at room temperature until all the amalgam disappears. The resulting product mixture comprising nitrosoeverninomicin and hydroxylaminoeverninomicin is then isolated by filtration and the products separated and purified utilizing known techniques such as recrystallization, reprecipitation, extraction, and chromatographic techniques. For example, a preferred species of our reduction process, i.e. that utilizing everninomicin D as starting antibiotic, is carried out by adding to a solution containing 4.5 grams purified everninomicin D in 100 ml. 95% ethanol and 85 ml. water, freshly prepared aluminum amalgam derived from 810 mg. of Reynolds Wrap aluminum foil, and stirring the mixture at room temperature until the amalgam has disappeared (about two hours) and filtering off the resulting product mixture comprising nitrosoeverninomicin D and hydroxylaminoeverninomicin D. The hydroxylaminoeverninomicin D is conveniently isolated from the product mixture via thin layer chromatographic techniques such as that described in detail in Example 1-D whereby the product mixture is chromatographed on silica gel preparative plates (2000 μ thick) using 50% acetone in benzene as developing solvent, followed by visualization of the plate under ultraviolet light, and removal of the band having an $R_f$ = 0.45 by means of acetone. Concentration of the acetone solution of the $R_f$ = 0.45 band yields purified hydroxylaminoeverninomicin D in about 33% yield having properties as set forth hereinbelow and in Example 1-D.

When isolating nitrosoeverninomicin D from the product mixture comprising hydroxylaminoeverninomicin D and nitrosoeverninomicin D, the product mixture is usually chromatographed on silica gel preparative plates (2000 μ thick) using acetone/ethyl acetate/benzene (2:2:1) as developing solvent, visualizing the plate under ultraviolet light, then extracting with acetone that band having an $R_f$ value in the range of 0.75–0.85, followed by concentration of the acetone extracts to yield nitrosoeverninomicin D in small yields, i.e. less than 1%.

Oxidation Process:

As described hereinabove, low yields of nitrosoeverninomicin are obtained when an everninomicin selected from the group consisting of everninomicin B, everninomicin C, and everninomicin D is reduced with aluminum amalgam. Accordingly, the process of choice for preparing nitrosoeverninomicin is via oxidation of the corresponding hydroxylaminoeverninomicin utilizing reagents such as aerial oxidation in alkaline solution (e.g. bubbling air through a solution of hydroxylaminoeverninomicin D is dilute aqueous sodium hydroxide) or with an alkali metal hypobromite (preferably sodium hypobromite) in an aprotic solvent, the latter being the preferred oxidizing reagent for this process.

Alkali metal hypobromites which are useful in our oxidation process include potassium hypobromite, lithium hypobromite, and preferably, sodium hypobromite. Aprotic solvents useful in our oxidation process include dioxane, diethylene glycol dimethyl ether (also called diglyme), methanol, ethanol, and preferably, tetrahydrofuran.

Our oxidation process is usually carried out by treating one gram of hydroxylaminoeverninomicin (e.g. hydroxylaminoeverninomicin D) in 10 ml. tetrahydrofuran with an equal volume (i.e. 10 ml.) of aqueous sodium hypobromite prepared as described in Organic Synthesis, COLL., Vol. 4, 45 (1963) and stirring the reaction mixture until the starting hydroxylaminoeverninomicin has disappeared as determined via thin layer chromatographic techniques. The nitrosoeverninomicin thereby produced (e.g. nitrosoeverninomicin D) is isolated from the reaction mixture by addition of water followed by extraction with a halogenated solvent, e.g. methylene chloride, and evaporation of the methylene chloride extracts to a residue comprising about 60% yield of nitrosoeverninomicin. Further purification can be effected utilizing thin layer chromatographic techniques similar to that described hereinabove for the purification of nitrosoeverninomicin D, whereby is isolated about a 60% yield of nitrosoeverninomicin D having physical characteristics as set forth in Example 2-A hereinbelow.

Composition-of-Matter Aspect

Included within the composition-of-matter aspect of this invention are everninomicin antibacterial derivatives selected from the group consisting of nitrosoeverninomicin B, nitrosoeverninomicin C, nitrosoeverninomicin D, hydroxylaminoeverninomicin B, hydroxylaminoeverninomicin C, hydroxylaminoeverninomicin D, nitrone derivatives of said hydroxylaminoeverninomicins B, C, and D, and pharmaceutically acceptable salts of the foregoing nitrosoeverninomicins and of the hydroxylaminoeverninomicins and their nitrones.

The above listed nitrosoeverninomicins, hydroxylaminoeverninomicins and nitrone derivatives of said hydroxylaminoeverninomicins all contain an acidic phenolic hydroxyl function which is readily convertible to pharmaceutically acceptable cationic salts thereof utilizing procedures known in the art.

Among the pharmaceutically acceptable cationic salts contemplated for this invention are salts of alkali and alkaline earth metals (e.g. sodium, potassium, clacium, aluminum) and salts with an amine selected from the group consisting of trialkylamines, procaine, dibenzylamine, N-benzyl-beta-phenethylamine, N,N'-dibenzylethylene-diamine, N,N'-bis-dehydroabietylethylenediamine and N-(lower)alkylpiperidines, e.g. N-ethylpiperidine. Also included within the term "pharmaceutically acceptable salts" are N-methyl glucamine salts of the nitrosoeverninomicins and of the hydroxylaminoeverninomicins and nitrone derivatives thereof.

The hydroxylaminoeverninomicin nitrone derivatives of our invention are derived from the corresponding hydroxylaminoeverninomicin (e.g. hydroxylaminoeverninomicin B, C, or D) by treatment in known manner with an aldehyde which may have an aliphatic, alicyclic or aromatic hydrocarbon radicals which may be substituted by oxygen, sulfur or nitrogen in a side chain or a hydrocarbon chain or ring forming heteroaldehyde. Our nitrone derivatives are thus derived from aliphatic aldehydes such as formaldehyde, acetaldehyde, propionaldehyde, heptanal, decanal, n-dodecanal, from alicyclic aldehydes such as cyclopropylaldehyde, cyclopentylaldehyde, cyclohexylaldehyde, 3-cyclohexylpropylaldehyde, from aromatic aldehydes such as benzaldehyde, p-hydroxybenzaldehyde, tolylaldehyde, 2-phenethylaldehyde, naphthylaldehyde, α-naphthylformaldehyde, and from hetero substituted aldehydes such as furfural, thienylaldehyde, thiazolaldehyde, pyrazinaldehyde, pyranylaldehyde, and the like. Our nitrone derivatives are preferably derived from aldehydes having hydrocarbon radicals or oxygen containing radicals including benzaldehyde, heptylaldehyde, and furfural.

The everninomicin B, C, and D reduction products of this invention are oligosaccharides, and each contains a dichloroisoeverninoyl ester grouping, a reduced evernitrose group (i.e. a group wherein the nitro function in evernitrose has been reduced to nitroso or hydroxylamino) or derivatives thereof, at least two ortho ester functions, and several anomerically linked monosaccharide groups.

It is known in the art that ortho esters hydrolyze readily and that hydroxylamino functions oxidize easily to a nitroso function. In view of the presence of these functions in our compounds, to minimize side reactions, it is preferable to store them under anhydrous conditions in an inert atmosphere (e.g. under nitrogen, argon, etc.) at cool temperatures (i.e. at about 5°–10° C).

Preferred compounds of our invention include those derived from everninomicin D and derivatives thereof, all of which possess antibacterial acitivity, being particularly effective in inhibiting the growth of gram-positive bacteria. Of these, hydroxylaminoeverninomicin D and the pharmaceutically acceptable salts thereof, particularly the sodium salt, are of special interest since they possess comparable antibacterial activity against gram-positive bacteria as that exhibited by the everninomicin D precursor; moreover, when administered by injection in the form of its sodium salt, hydroxylaminoeverninomicin D is advantageously more rapidly absorbed, producing higher serum levels, and more rapidly excreted than everninomicin D. Advantageously, certain gram-negative bacteria are also susceptible to (i.e. their growth is inhibited by) hydroxylaminoeverninomicin D.

Included among the preferred everninomicin D reduction products of our invention are compounds defined by structural formula I shown hereinabove and the pharmaceutically acceptable salts thereof wherein Y is hydrogen, Z is $$-CH\begin{matrix}CH_3\\ \\OCH_3\end{matrix}$$

and X is a member selected from the group consisting of nitroso (i.e. X is —N=O), hydroxylamino (i.e. X is

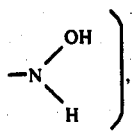

and a hydroxylamino nitrone derivative (i.e. wherein X is

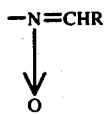

wherein R is a hydrocarbon which may be substituted by oxygen, sulfur, or nitrogen.

The compound of formula I wherein Y is hydrogen, Z is

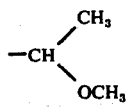

and X is —N=O is nitrosoeverninomicin D; the compound of formula I wherein Y is hydrogen, Z is

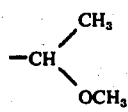

and X is

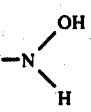

is hydroxylaminoeverninomicin D, and those compounds of formula I wherein Y is hydrogen, Z is

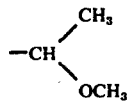

and X is

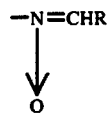

are hydroxylaminoeverninomicin D nitrone derivatives including hydroxylaminoeverninomicin D benzyl nitrone (derivative wherein R is phenyl); hydroxylaminoeverninomicin D furfuryl nitrone (derivative wherein R is furfuryl); and hydroxylaminoeverninomicin D heptyl nitrone (derivative wherein R is hexyl).

The pharmaceutically acceptable salts of the compounds of our invention include those which replace the phenolic hydrogen with a cation (e.g. hydroxylaminoeverninomicin D sodium salt) and those wherein the phenolic hydrogen and everninomicin radical forms an acid addition salt with an amine (e.g. nitrosoeverninomicin D N-methylglucamine salt).

Other pharmaceutically acceptable salts of our invention are:
 hydroxylaminoeverninomicin D sodium salt;
 hydroxylaminoeverninomicin D N-methylglucamine salt;
 hydroxylaminoeverninomicin D benzyl nitrone sodium salt;
 hydroxylaminoeverninomicin D benzyl nitrone N-methylglucamine salt;
 hydroxylaminoeverninomicin D heptyl nitrone sodium salt;
 hydroxylaminoeverninomicin D heptyl nitrone N-methylglucamine salt;
 hydroxylaminoeverninomicin D furfuryl nitrone sodium salt; and
 hydroxylaminoeverninomicin D furfuryl nitrone N-methylglucamine salt.

The pharmaceutically acceptable cationic salts (e.g. the sodium salt) are prepared according to known procedures such as by combining equimolar quantities of the corresponding base (e.g. sodium hydroxide) to the everninomicin derivative (e.g. hydroxylaminoeverninomicin D) in an aqueous solution and lyophilizing the resultant solution of the hydroxylaminoeverninomicin D salt.

The pharmaceutically acceptable salts of our invention are white amorphous solids which are water soluble and form stable aqueous solutions. They are, therefore, a particularly preferred species of our invention since they are a convenient vehicle for administering the nitrosoeverninomicins and hydroxylaminoeverninomicins of our invention. A particularly valuable species of our invention is hydroxylaminoeverninomicin D sodium salt.

The nitrosoeverninomicins B, C and D and hydroxylaminoeverninomicins B, C and D of this invention including derivatives and pharmaceutically acceptable salts thereof, particularly the preferred group of compounds of our invention, i.e. nitrosoeverninomicin D, hydroxylaminoeverninomicin D, and nitrones thereof, and pharmaceutically acceptable salts of the foregoing, exhibit a narrow spectrum antibacterial activity in vitro against gram-positive bacteria (e.g. *Staphylococcus aureus*, Staph. 11631, Staph. W., *Streptococcus pyogenes* C, *Strep. pyogenes* C-203 and *Bacillus subtilis*) and against certain gram-negative bacteria (e.g. *Neisseria gonorrhea* and *Neisseria meningitidis*). Our compounds are thus advantageously employed as laboratory reagents when attempting to determine the presence of enteric gram-negative organisms. They may be used to inhibit overgrowth of such organisms in culture media, either alone or in combination with other antibacterial agents to reduce or eliminate the heavy overgrowth of gram-positive organisms permitting the determination of gram-negative organisms such as *Klebsiella pneumoniae* or *Escherichia coli* in cultures obtained in diagnostic procedures. As such reagents they may be employed in solution.

In view of their action against gram-positive and gram-negative organisms, the antibacterials described herein may be used to "sterilize" equipment such as in operating rooms and in hospital wards.

The comparative in vitro activities of nitrosoeverninomicin D and the sodium salt thereof, hydroxylaminoeverninomicin D and the sodium salt and N- methylglucamine salt thereof, hydroxylaminoeverninomicin D benzyl nitrone N-methylglucamine salt, hydroxylaminoeverninomicin B and hydroxylaminoeverninomicin C are set forth in Table 1 below.

The susceptibility of the test gram-positive microorganisms to the antibacterials was determined by standard tube dilution methods. In each instance $10^{-5}$ dilutions of 24-hour broth cultures were employed as inoculum with the endpoints being taken after incubation for 24 hours at 37° C in a Difco Penassy broth medium (Difco Labs., Detroit, Michigan). In the tables, the activity (or assay value) of each respective antibacterial agent is expressed in units per milliliter or micrograms per milliliter.

The microbiological assay (also called the bioassay) is effected microbiologically by a standard cup-type agar diffusion assay technique using S. aureus (A.T.C.C. 6538p) as test organism. A reference curve is prepared by plotting the dosage-response of the antibacterial agent in ethanol diluted by phosphate buffer at pH7 upon a medium of the following composition which has been inoculated with the test organism (i.e. S. aureus):

|  | Percent |
|---|---|
| Peptone | 0.6 |
| Pancreatic digest of casein | 0.4 |
| Yeast extract | 0.3 |
| Beef extract | 0.15 |
| Dextrose | 0.15 |
| Agar | 1.5 |
| pH, 6.6 | |

A suspension of the assay organism (S. aureus A.T.C.C. 6538p) is standardized to produce 20% transmission at 660 m$\mu$ in a colorimeter. The potency of the sample is determined from the reference curve and expressed in terms of units per milligram (a unit being that amount of test substance required to produce a 15 mm zone of inhibition with a steel cylinder of 6.5 mm outside diameter).

The susceptibility of the gram-negative microorganisms to the antibacterials was determined by plate dilution methods in Thayer-Martin medium by the known Thayer-Martin procedure.

In above Table 1, there is also listed in vivo data for the peak serum levels in dogs and rats, as well as $PD_{50}$ and $LD_{50}$ doses in mice for everninomicin D and reduced derivatives thereof, against Staphylococcus and Streptococcus.

The acute toxicity ($LD_{50}$) of the antibacterial substances in either aqueous suspensions or aqueous solutions is measured in milligrams per kilogram in standard manner using male CF-1 mice weighing 20 grams.

The protection tests to determine the dose required to protect fifty percent of the animals tested ($PD_{50}$) use groups of seven mice (male albino CF-1 mice, each weighing 18–20 g.) each at five dose levels with 10 mice serving as controls. Mice were each treated with a single subcutaneous or oral dose one hour after intraperitoneal infection with approximately $10^7$ organisms. Control mice were generally dead 18–24 hours after infection. Survivors in treated groups were determined 48 hours after infection. Probit procedures were used to determine $PD_{50}$ values in milligrams per kilogram.

In determining peak serum levels, the animal tested (e.g. dog or rat) is given a single dose of 10 or 25 mg/kg of everninomicin D or derivative thereof of this invention, blood samples are taken periodically, and the serum thereof is assayed for anti-bacterial activity by an agar-diffusion-assay as described by Weinstein et al., Antimicrobial Agents and Chemotherapy, p 24 (1964).

It is apparent from the foregoing data that, when administered by injection in the form of its sodium salt, hydroxylaminoeverninomicin D exhibits antibacterial activity comparable to that of the everninomicin D precursor and, advantageously, is more rapidly absorbed producing higher serum levels (i.e. 20–30) in the dog than that produced by everninomicin D (i.e. 2–3).

We have described in detail the preferred species of our invention relating to hydroxylaminoeverninomicin D derivatives. In similar manner, our invention is carried out to produce anti-bacterial substances which are derivatives of everninomicin B and everninomicin C. Thus, an everninomicin antibiotic mixture produced when Micromonospora carbonacea var. carbonacea or varient thereof is subjected to submerged aerobic fermentation according to known procedures. Said everninomicin mixture, comprising everninomicin B, ever-

TABLE 1

EVERNINOMICIN DERIVATIVES

| | Everninomicin D | Hydroxylaminoeverninomicin D | Sodium salt and N-methylglucamine salt minoeverninomicin D | Nitrosoeverninomicin D | Sodium salt of nitroeverninomicin D | N-methylglucamine salt of hydroxylaminoeverninomicin D benzyl nitrone | Hydroxylaminoeverninomicin C | Hydroxylaminoeverninomicin B |
|---|---|---|---|---|---|---|---|---|
| MIC (mcg/ml)[a] | 0.03–0.3 | 0.3–0.8 | 0.08–0.8 | 0.08–0.8 | 0.08–3 | | 0.1–1 | 0.1–0.8 |
| MIC (mcg/ml)[b] | | | 0.2–1.0 | | | | | |
| $PD_{50}$[a] mg/kg Oral | 15 | | 25 | | — | | | |
| S.C. | 5 | 0.5–5 | | — | | | | |
| $LD_{50}$[a] in mice I.P. | >3800 | | 500 | | — | | | |
| (mg/kg) S.C. | >3800 | | 500 | | — | | | |
| Oral | >3800 | | >2000 | | — | | | |
| I.V. | 125 | 30 | | — | | | | |
| Peak serum levels in dogs (mcg/ml) | | | | | | | | |
| 10 mg/kg I.M. | 2–3 | | 20–30 | 6 | | 1–2 | | 15 |
| Peak serum levels in rats (mcg/ml) | | | | | | | | |
| 25 mg/kg S.C. | 10–12 | | 30–40 | 10–11 | | 10–12 | | 9 |

[a]Staphylococcus and Streptococcus
[b]N.gonorrhea and N.meningitidis ninomicin C and everninomicin D, is purified and the B, C, and D components are separated utilizing chromatograhic techniques such as described hereinbelow in Example 8. The purified everninomicin B and everninomicin C, respectively, having the physical constants set forth in Examples 8C(3) and 8C(2), respectively, are then reduced with aluminum amalgam in an alcohol-aqueous mixture according to our process to produce hydroxylaminoeverninomicin C, respectively, having antibacterial activity as evidenced by data set forth in Table I determined by standard in vitro and in vivo tests discussed hereinabove. Upon oxidizing the hydroxylaminoeverninomicin B and C derivatives thereby produced with sodium hypobromite in tetrahydrofuran by the oxidation process of this invention, there is obtained nitrosoeverninomicin B and nitrosoeverninomicin C, respectively. Nitrone derivatives of hydroxylaminoeverninomicin B and C having anti-bacterial activity are derived as described herein by treatment of the respective hydroxylaminoeverninomicin with an aldehyde. Salts of hydroxylaminoeverninomicin B and C including cationic salts, amine salts, and N-methylglucamine salts, are prepared in manner similar to that described for everninomicin D.

As discussed hereinabove, the everninomicin B, C, and D reduction products of this invention exhibit antibacterial activity against gram-positive bacteria and against certain gram-negative bacteria. Advantageously, our everninomicin B, C, and D reduction products exhibit antibacterial activity aganist bacteria which are resistant to other antibacterial agents such as penicillin, penicillinase - resistant penicillins, tetracycline, macrolide antibacterials such as erythromycin, and lincomycin.

Procedures are set forth hereinbelow to illustrate the best mode contemplated by applicants for carrying out their invention and are not to be construed as limiting the scope thereof.

EXAMPLE 1

Reduction of Everninomicin D to Hydroxylaminoeverninomicin D

A. Purification of Everninomicin D

1. Everninomicin D, the requisite intermediate, is prepared by cultivating a micro-organism selected from the group consisting of *Micromonospora carbonacea var. carbonacea* NRRL 2972 and *Micromonospora carbonacea var. aurantiaca* NRRL 2992 under submerged aerobic conditions in an aqueous nutrient medium containing an assimilable source of carbon and nitrogen and isolating everninomicin D from the antibiotic mixture thereby produced by procedures described in U.S. Pat. No. 3,499,078.

2. Treat a solution of 66 g. of everninomicin D (prepared as described in paragraph 1 hereinabove) in 300 ml. of acetone with 7 g. of charcoal at room temperature. Filter and wash the charcoal with 100 ml. of acetone. Pour the combined acetone filtrate and washes onto a solution of 10.5 liters of petroleum ether (b.p. 60° C) and 2.7 liters of ethly ether. Filter and dry the resultant precipitate of everninomicin D.

3. Further purify the thus obtained everninomicin D (about 56 grams) by reprecipitating an acetone (250 ml.) solution thereof with about 10 liters of a solvent mixture comprising petroleum ether/ethyl ether (4:2). Filter and dry the resultant precipitate of everninomicin D to a constant weight at 60° C (yield about 52 grams).

4. Further purify 30 g. of the everninomicin D obtained as described above in a minimum amount of acetone, add 120 g. of fresh silica gel, then evaporate the solvent at 60° C until a constant weight is obtained. Add this mixture to the top of a 5 ft. by 1¾ inch chromatographic column charged with 450 g. of silica gel made up in benzene. Elute the column first with about 7 liters of a solvent mixture comprising 15% acetone-85% benzene, followed by elution with a solvent mixture comprising 20% acetone-80% benzene. Collect 1 liter fractions, monitoring the fractions by thin layer chromatography. Concentrate pooled fractions 8–16 in vacuo at 50° C to a residue comprising everninomicin D (about 18g.) having an $R_f$ of 0.79 via thin layer chromatography in a 60% acetone-40% benzene system.

Molecular Formula: $C_{66}H_{99}O_{35}NCl_2$; Molecular Weight: 1537(calc.)

| Combustion Analysis: | Found | Calc. |
|---|---|---|
| Carbon | 51.64% | 51.56 |
| Hydrogen | 6.57% | 6.49 |
| Nitrogen | 0.83% | 0.91 |
| Chlorine | 4.38% | 4.61 |

Specific Optical Rotation: $[\alpha]_D^{26}$ −34.2° (chloroform)
Neutralization Equivalent: 1563 (calc. for $C_{66}H_{99}O_{35}NCl_2$: 1537).
pKa: 7.2

5. Store everninomicin D under an atmosphere of nitrogen at about 5° C.

B. Preparation of Aluminum Amalgam

To Reynolds Wrap Aluminum Foil (cut into peices of about 0.5 cm. Square), add dilute sodium hydroxide until there is a strong evolution of hydrogen gas. Decant the dilute sodium hydroxide and wash once superficially with water. Decant the water wash and add a 0.5% mercuric chloride solution allowing aluminum to remain in the solution for about one to two minutes. Decant the mercuric chloride solution. Repeat the entire foregoing procedure, then wash the shiny amalgamated aluminum in turn with water, ethanol, then ether and use immediately in following Example 1-C.

C. Reduction of Everninomicin D

To a solution of 4.5 g. of everninomicin D (purified as described in Example 1-A) in 100 ml. of 95% ethanol and 85 ml. of water, add with stirring at room temperature aluminum amalgam prepared from 810 mg. of Reynolds Wrap Aluminum Foil as described in Example 1-B. Stir the reaction mixture at room temperature until all the amalgam disappears (approximately 2 hours). Filter the gray reaction mixture on a Buchner funnel using a filter pad and wash the insoluble residue with 95% ethanol. Combine the filtrate and ethanol washings and concentrate to a volume of approximately 100 ml. Cool the concentrate in an ice bath for about an hour; separate by filtration the resulting insoluble fraction comprising 2.9 g. of hydroxylaminoeverninomicin D; dry the insoluble fraction in vacuo at room temperature prior to further purification.

D. Purification of Hydroxylaminoeverninomicin D

Purify the crude hydroxylaminoeverninomicin D (2.9 g.) obtained as described in Example 1-C using 20 silica gel preparative plates (2000 μ thick) and using 50% acetone in benzene as the developing solvent.

Visualize the purified hydroxylaminoeverninomicin D ($R_f$=0.45) using ultraviolet light and extract the purified hydroxylaminoeverninomicin D band (i.e. the 0.45 $R_f$ band) from the plate using acetone. Combine the acetone extracts and distill to a residue comprising 1.5 g. of purified hydroxylaminoeverninomicin D having the following properties:

Molecular Formula: $C_{66}H_{101}O_{34}NCl_2$; Molecular Weight: 1523 (calc.) m.p.: 190–200°C Kofler block;

| Combustion Analysis | Found | Calc. |
|---|---|---|
| Carbon | 51.81% | 52.05 |
| Hydrogen | 6.64% | 6.68 |
| Nitrogen | 0.59% | 0.92 |
| Chlorine | 4.55% | 4.66 |

Specific optical rotation: $[\alpha]_D^{26}$ −39.3° (chloroform);
Ultraviolet absorption:
$\lambda_{max}$ methanol 215 m$\mu$, $\epsilon_1^1$, 19.2
        292 m$\mu$, $\epsilon_1^1$, 3.4

Infrared absorption spectrum in chloroform: 2.92, 5.80, 6.37, 6.92, 7.13, 7.26, 8.06, (broad), broad absorption between 9.13 and 9.70 microns (see FIG. 1).

In this specification, when reporting ultraviolet absorption data, by "$\xi$" is meant "$\xi_{cm.}$%" which is defined as the optical density of a 1% solution of a compound measured in a 1 centimeter cell.

Nuclear magnetic resonance spectrum in deuterochloroform: (See FIG. 2).

EXAMPLE 2

Nitrosoeverninomicin D

A. Preparation by Oxidation of Hydroxylaminoeverninomicin D

The reagent sodium hypobromite is prepared according to the procedure described in Organic Synthesis, COLL., Vol. 4, 45 (1963).

To 1 millimole (1 mmol) of a solution of hydroxylaminoeverninomicin D in solution in tetrahydrofuran (1 g. dissolved in 10 ml. of tetrahydrofuran), add 1 mmol of aqueous sodium hypobromite solution at room temperature. Follow the course of the reaction by thin layer chromatography (silica gel plates 250 $\mu$; solvent system acetone/ethyl acetate/benzene [2:2:1]). After the starting material has disappeared, add water to the reaction mixture and extract with methylene chloride. Evaporate the combined methylene chloride. Evaporate the combined methylene chloride extracts to a residue comprising nitrosoeverninomicin D (yield about 60% theory) which is further purified as described hereinbelow.

Chromatograph 100 mg. of nitrosoeverninomicin D on a thin layer chromatographic preparative plate (2000 $\mu$ thick) using acetone/ethyl acetate/benzene (2:2:1) as the developing solvent. Visualize the purified nitrosoeverninomicin D by means of ultraviolet light and extract from the plate with acetone the band in the approximate $R_f$ range of 0.75–0.85. Evaporate the combined acetone extracts to a residue comprising about 60 mg. of nitrosoeverninomicin D having the following properties:
Molecular Formula: $C_{66}H_{99}O_{34}NCl_2$; Molecular Weight: 1521 (Calc'd).
163°–165° C Kofler block

| Combustion Analysis: | Found | Calc. |
|---|---|---|
| Carbon | 51.66% | 52.11 |
| Hydrogen | 6.52% | 6.56 |
| Nitrogen | 0.84% | 0.92 |
| Chlorine | 4.50% | 4.66 |

Specific Optical Rotation: $[\alpha]_D^{26}$ −30.8 (chloroform);
Ultraviolet Absorption Spectrum:
$\lambda_{max}$ methanol 212 m$\mu$, $\epsilon_1^1$, 16.05
        292 m$\mu$, $\epsilon_1^1$, 5.60

Infrared Absorption Spectrum in chloroform: 2.9, 3.4, 5.8, 6.4, 6.5, 6.9, 7.2, 9.0, 9.6, 10.2, 10.5 microns (See FIG. 3).

Nuclear Magnetic Resonance Spectrum: (See FIG. 4).
Bioassay: 1460 $\gamma$/ml.

B. Preparation by Reduction of Everninomicin D

In a manner similar to that described in Example 1-C, treat everninomicin D in aqueous ethanol with aluminum amalgam and isolate the resultant product comprising nitrosoeverninomicin D in admixture with hydroxylaminoeverninomicin D.

Isolate the purify the nitrosoeverninomicin D using 20 silica gel preparative plates (2000 $\mu$ thick) and using acetone/ethyl, acetate/benzene (2:2:1) as the developing solvent. Visualize the purified nitrosoeverninomicin D ($R_f$ about 0.78) using an ultraviolet light. Extract the 0.78 $R_f$ band from the plate using acetone. Combine the acetone extracts and distill in vacuo to a residue of nitrosoeverninomicin D.

EXAMPLE 3

Hydroxylaminoeverninomicin D Benzyl Nitrone

To 400 mg. of hydroxylaminoeverninomicin D in 15 ml. of anhydrous ethanol, add 0.2 ml. of benzaldehyde. Stir at room temperature for 72 hours, then distill in vacuo to a residue. Triturate the residue with hexane and separate by filtration and air dry the resultant precipitate comprising hydroxylaminoeverninomicin D benzyl nitrone.

Purify via thin layer chromatographic techniques using silica gel with acetone/benzene (1:1) as the developing solvent. Visualize the benzyl nitrone derivative using ultraviolet light and extract with acetone the band within the $R_f$ zone of from about 0.5 to about 0.7. Evaporate the acetone in vacuo to a residue of 200 mg. of purified hydroxylaminoeverninomicin D benzyl nitrone as a colorless solid having the following characterizing data:
m.p.: 168°–170° C Kofler block;
Molecular Formula: $C_{73}H_{105}NO_{34}Cl_2$; Molecular Weight: 1611 (Calc.)

| Combustion Analysis: | Found | Calc. |
|---|---|---|
| Carbon | 53.34% | 54.42 |
| Hydrogen | 7.01% | 6.57 |
| Nitrogen | 0.74% | 0.87 |
| Chlorine | 3.94% | 4.40 |

Specific Optical Rotation: $[\alpha]_D^{26}$ −67° (chloroform);
Ultraviolet Absorption Spectrum:
$\lambda_{max}$ methanol 295 m$\mu$, $\epsilon_1^1$, 1495;

Infrared Absorption Spectrum in chloroform: 2.9, 3.4, 5.75, 5.8, 6.35, 6.9, 7.2, 9.1, 9.6, 10.5, 11.0 microns (See FIG. 5).
Bioassay: 1309.0 γ/ml.

EXAMPLE 4

Hydroxylaminoeverninomicin D Furfuryl Nitrone

To 375 mg. of hydroxylaminoeverninomicin D in 25 ml. of anhydrous ethanol, add 1 ml. of 2-furancarbonal (2-furfuraldehyde). Stir at room temperature overnight then distill in vacuo to a residue. Triturate the residue with hexane and dry the resultant precipitate comprising hydroxylaminoeverninomicin D furfuryl nitrone.

Purify via preparative thin layer chromatography utilizing silica gel with acetone/benzene (1:1) as the developing solvent. Visualize the furfuryl nitrone derivative by means of ultraviolet light and extract with acetone that band having an $R_f$ in the range of from about 0.75 to about 0.85. Concentrate the acetone solution in vacuo to obtain 186 mg. (50% yield) of hydroxylaminoeverninomicin D furfuryl nitrone having the following characterizing data:
m.p.: 173°–175° C Kofler block;
Molecular Formula: $C_{71}H_{103}NO_{35}Cl_2 \cdot 2H_2O$; Molecular Weight: 1637 (Calc.)

| Combustion Analysis: | Found | Calc. |
|---|---|---|
| Carbon | 51.81% | 52.09 |
| Hydrogen | 6.70% | 6.59 |
| Nitrogen | 0.74% | 0.86 |
| Chlorine | 4.04% | 4.33 |

Specific Optical Rotation: $[\alpha]_D^{26}$ −63.2° (chloroform); Ultraviolet Absoprtion Spectrum:
$\lambda_{max}^{methanol}$ 302 mμ, $\epsilon_1^1$, 18.35;
Bioassay: Absorption Spectrum; 2.9, 3.4, 5.8, 6.2, 6.3, 6.8, 7.2, 8.0, 9.0, 9.6, 10.5, 10.9 microns, (See FIG. 6).
Bioassay: 1063.4 γ/ml.

EXAMPLE 5

Hydroxylaminoeverninomicin D Heptyl Nitrone

To 375 mg. of hydroxylaminoeverninomicin D in 25 ml. of anhydrous ethanol, add 1 ml. of heptaldehyde. Stir at room temperature overnight, then distill the solvent in vacuo to a residue. Triturate the residue with hexane and separate by filtration and air dry the resultant solid comprising hydroxylaminoeverninomicin D heptyl nitrone to give 280 mg. (75% theoretical yield) of a colorless solid having the following characterizing data:
m.p.: 159°–160° C Kofler block;
Molecular Formula: $C_{73}H_{113}NO_{34}Cl_2$; Molecular Weight: 1619 (Calc.)

| Combustion Analysis: | Found | Calc. |
|---|---|---|
| Carbon | 54.15% | 54.12 |
| Hydrogen | 7.44% | 7.03 |
| Nitrogen | 0.72% | 0.86 |
| Chlorine | 3.84% | 4.38 |

Specific Optical Rotation: $[\alpha]_D^{26}$ −46.0° (chloroform); Ultraviolet Absorption Spectrum:
$\lambda_{max}^{methanol}$ 295 mμ, $\epsilon_1^1$, 5.25;

Infrared Absorption Spectrum in Chloroform: 2.9, 3.5, 5.7, 6.3, 6.9, 7.2, 9.0, 9.6, 10.5, 10.9 microns (See FIG. 7).
Bioassay: 892 γ/ml.

EXAMPLE 6

Sodium Salt of Hydroxylaminoeverninomicin D and Derivatives Thereof

A. To a vigorously stirred suspension of 1 g. of hydroxylaminoeverninomicin D in 25 ml. of water under a nitrogen atmosphere, slowly add 0.1 N-sodium hydroxide (about 6.8 ml.) until the pH of the reaction mixture is 9.5 and the solid is in solution. Stir at room temperature for an additional hour (final pH about 8.5). Lyophilize the clear solution to obtain 0.95 g. of hydroxylaminoeverninomicin D sodium salt as a white solid.

B. In the above procedure by substituting for the sodium hydroxide equimolar quantities of other alkaline metal hydroxides (e.g. potassium hydroxide and lithium hydroxide) or by alkaline earth metal hydroxides (e.g. calcium hydroxide and barium hydroxide), there is obtained the corresponding alkali metal or alkaline earth metal salt, e.g. hydroxylaminoeverninomicin D potassium salt, hydroxylaminoeverninomicin D lithium salt, hydroxylaminoeverninomicin D calcium salt and hydroxylaminoeverninomicin D barium salt, respectively.

C. In a manner similar to that described in Example 6-A hereinabove, treat each of the following compounds with 0.1 N-sodium hydroxide:
nitrosoeverninomicin D;
hydroxylaminoeverninomicin D benzyl nitrone;
hydroxylaminoeverninomicin D furfuryl nitrone; and
hydroxylaminoeverninomicin D heptyl nitrone.
Isolate the resultant product in a manner similar to that described in Example 6-A to obtain, respectively,
nitrosoeverninomicin D sodium salt;
hydroxylaminoeverninomicin D benzyl nitrone sodium salt;
hydroxylaminoeverninomicin D furfuryl nitrone sodium salt; and
hydroxylaminoeverninomicin D heptyl nitrone sodium salt.

EXAMPLE 7

N-Methyl Glucamine Salt of Hydroxylaminoeverninomicin D and Derivatives Thereof

A. To 300 mg. of hydroxylaminoeverninomicin D dissolved in 1.5 ml. of methanol, add 40 mg. of N-methyl glucamine and stir the reaction mixture at room temperature for 1 ½ hours. Slowly add ether (40 ml.) with good agitation. Separate the resultant precipitate by filtration and air dry to give 175 mg. of hydroxylaminoeverninomicin D N-methyl glucamine as a white solid.

Similarly, treat each of the following with N-methyl glucamine in methanol:
nitrosoeverninomicin D;
hydroxylaminoeverninomicin D benzyl nitrone;
hydroxylaminoeverninomicin D furfuryl nitrone; and
hydroxylaminoeverninomicin D heptyl nitrone.
Isolate the resultant product in a manner similar to that described hereinabove to obtain, respectively,
nitrosoeverninomicin D N-methyl glucamine salt;

hydroxylaminoeverninomicin D benzyl nitrone N-methyl glucamine salt;

hydroxylaminoeverninomicin D furfuryl nitrone N-methyl glucamine salt; and hydroxylaminoeverninomicin D heptyl nitrone N-methyl glucamine salt.

EXAMPLE 8

Preparation and Purification of Everninomicin B, Everninomicin C, and Everninomicin D A. Preparation of Antibiotic Mixture Comprising Everninomicin B, Everninomicin C, and Everninomicin D In the manner described in U.S. Pat. No. 3,499,078, Example 1, prepare a 500 gallon fermentation broth by cultivating a micro-organism selected from the group consisting of *Micromonospora carbonacea var. carbonacea* NRRL 2972 and *Micromonospora carbonacea var. Aurantiaca* NRRL 2992 under submerged aerobic conditions in an aqueous nutrient medium containing an assimilable source of carbon and nitrogen. Extract 500 gallons of fermentation broth with 500 gallons of methylene chloride, then concentrate the methylene chloride extracts in vacuo to a residue having a volume of about 3 liters. Pour the residue into 30 liters of hexane, then filter and air dry the resultant precipitate comprising a mixture of everninomicin B, everninomicin C, and everninomicin D.

B. Separation of Antiobiotic Mixture

Prepare the chromatographic column by making a slurry of 11.35 kg. of silica gel (Bakers) in benzene/acetone (60:40). Then transfer the slurry into two 5 ft. × 4 in. columns and allow the columns to settle over night. Place the two columns in series so they will act as one continuous column.

Dissolve 300 g. of the mixture of everninomicin B, C and D prepared as described in Example 8A in about 1 liter of benzene/acetone (60:40) with vigorous stirring. Transfer this solution onto the columns.

Elute the column (i.e. the two columns in series) with benzene/acetone (60:40) and collect 1800 ml. fractions. Combine like fractions as determined by thin layer chromatographic analysis (silica gel; benzene; acetone (60:40)). Then evaporate the combined fractions to a residue comprising everninomicin D, everninomicin C and everninomicin B, respectively, as follows: Fractions 14–18 yield a residue comprising 76.9 g. of everninomicin D; fraction 21 yields a residue comprising 5 g. everninomicin C and combined fractions 22–27 yield a residue comprising 29.5 g. of everninomicin B.

C. Purification of Everninomicin D,C, and B, respectively

1. Everninomicin D

Purify the residue of fractions 14–18 obtained in above Example 8B in a manner similar to that described in Example 1A to obtain purified everninomicin D having the physical constants set forth in Example 1A (4).

2. Everninomicin C

Crystallize the residue of fraction 21 obtained as described in Example 8B from ethyl acetate to obtain purified everninomicin C having the following properties:

Molecular Formula: $C_{63}H_{93}O_{34}NCl_2$ m.p.: 181°–184° C Kofler block;

| Combustion Analysis: | Found | Calc. |
|---|---|---|
| Carbon | 52.07 | 51.56% |
| Hydrogen | 6.44 | 6.49 |
| Nitrogen | 0.51 | 0.91 |
| Chlorine | 4.72 | 4.61 |

Specific Optical Rotation: $[\alpha]_D^{26}$ −33.7° (chloroform);
Ultraviolet Absorption:

$\lambda_{max}$ methanol 208 m$\mu$, $\epsilon_1^1$, 19.8
211 m$\mu$, $\epsilon_1^1$, 19.5

Infrared Absorption Spectrum in chloroform: 2.9, 3.4 (broad), 5.75, 6.32, 6.45, 6.85, 7.1, 7.2, 7.4, 7.7, 8.0, 9.0, 9.6, 10.2, and 11.0 microns (See FIG. 8).

3. Everninomicin B

Chromatograph 28 g. of everninomicin B prepared as described in above Example 8B (i.e. the residue from fractions 22 to 27) on 900 g. of silica gel G (TLC Grade; according to Stahl) eluting with 34% acetone in benzene. Collect 20 ml. fractions and combine like fractions as determined by thin layer chromatographic analysis. Evaporate combined fractions 211 to 310 in vacuo to a residue comprising purified everninomicin B (12.6 g.) having the following properties:

Molecular Formula: $C_{66}H_{99}O_{36}NCl_2$; Molecular Weight: 1553 (calc.)

m.p.: 184–185° C Kofler block

| Combustion Analysis: | Found | Calc. | (for $C_{66}H_{99}O_{36}NCl_2 \cdot 2H_2O$) |
|---|---|---|---|
| Carbon | 50.07% | 49.88 | |
| Hydrogen | 6.50% | 6.53 | |
| Nitrogen | 0.73% | 0.88 | |
| Chlorine | 4.24 | 4.46 | |

Specific Optical Rotation: $[\alpha]_D^{26}$ −33° (chloroform)
Ultraviolet Absorption Spectrum:

$\lambda_{max}$ methanol 210 m$\mu$, $\epsilon_1^1$, 17
285 m$\mu$, $\epsilon_1^{\ 1}$, 1.5

Infrared Absorption Spectrum (in chloroform): 2.9, 3.4, 5.75, 6.3, 6.45, 6.85, 7.20, 8.0, 8.5, 9.0, 9.6, 10.2, and 10.5 microns.

EXAMPLE 9

Reduction of Everninomicin C to Hydroxylaminoeverninomicin C

A. In a manner similar to that described in Example 1C, treat everninomicin C (prepared and purified as described in Example 8) in aqueous ethanol with aluminum amalgam. Isolate the resultant product in a manner similar to that described to obtain hydroxylaminoeverninomicin C.

B. Purify the crude hydroxylaminoeverninomicin C obtained as described in above Example 9A in a manner similar to that described in Example 1D using silica gel preparative plates (2000 $\mu$ thick) and using 50% acetone-benzene as the developing solvent. Visualize the purified hydroxylaminoeverninomicin C ($R_f$ =

0.27) with ultraviolet light and extract the purified hydroxylaminoeverninomicin C band from the plate using acetone. Combine the acetone extract and distill to a residue comprising purified hydroxylaminoeverninomicin C having the following properties:
Molecular Formula: $C_{63}H_{95}O_{33}NCl_2$
m.p.: 165–168° C Kofler block:

| Combustion Analysis | Found | | Calc'd |
| --- | --- | --- | --- |
| Carbon | 51.35, | 51.74% | 51.64% |
| Hydrogen | 6.66, | 6.75% | 6.54 |
| Nitrogen | 0.93, | 1.09% | 0.96 |
| Chlorine | 5.75% | | 4.84 |

Specific Optical Rotation: $[\alpha]_D^{26}$ −21.6° (methanol)
Ultraviolet Absorption Spectrum:
$\lambda_{max}$ methanol 212 m$\mu$, $\epsilon_1^1$, 17.32 methanol 290 m$\mu$, $\epsilon_1^1$, 3.33.
max
Infrared Absorption Spectrum (in chloroform): 2.9, 3.4, 5.8, 6.9, 7.2, 8.0, 9.1, 9.6, 10.25, and 11.0 microns (See FIG. 9).

C. In a manner similar to that described in Example 6, treat hydroxylaminoeverninomicin C with sodium hydroxide to obtain hydroxylaminoeverninomicin C sodium salt.

D. In a manner similar to that described in Example 7, treat hydroxylaminoeverninomicin C in methanol with N-methylglucamine to obtain hydroxylaminoeverninomicin C N-methylglucamine.

EXAMPLE 10

Reduction of Everninomicin B to Hydroxylaminoeverninomicin B

A. In a manner similar to that described in Example 1C treat everninomicin B (prepared and purified as described in Example 8) in aqueous ethanol with aluminum amalgam. Isolate and purify the resultant product in a manner similar to that described in Example 1C to obtain a product comprising hydroxylaminoeverninomicin B.

B. In a manner similar to that described in Example 1D, purify the crude hydroxylaminoeverninomicin B prepared in above Example 10A using silica gel preparative plates (2000 $\mu$ thick) and using 50% acetone in benzene as the developing solvent. Visualize the purified hydroxylaminoeverninomicin B ($R_f$ = 0.18) using ultraviolet light and extract the purified hydroxylaminoeverninomicin B band from the plate using acetone. Combine the acetone extracts and distill to a residue comprising purified hydroxylaminoeverninomicin B having the following properties:
Molecular Formula: $C_{66}H_{101}O_{35}NCl_2$; Molecular Weight: 1535 (Calc.)
m.p.: 171–173° C Kofler block

| Combustion Analysis: | Found: | Calc. | (for $C_{66}H_{101}O_{35}NCl_2 \cdot 4H_2O$) |
| --- | --- | --- | --- |
| Carbon | 49.61% | 50.3 | |
| Hydrogen | 6.63% | 6.97 | |
| Nitrogen | 1.00% | 0.89 | |
| Chlorine | | | |

Specific Optical Rotation: $[\alpha]_D^{26}$ −19.9 (methanol)

Ultraviolet Absorption Spectrum:
methanol 215 m$\mu$ $\epsilon_1^1$, 17.15
$\lambda_{max}$   299 m$\mu$ $\epsilon_1^1$, 3.15
Infrared Absorption Spectrum in chloroform: 2.9, 3.4, 5.8, 6.35, 6.9, 7.2, 8.0, 9.1 (broad -S), 9.6 (broad-S), 10.5, 11.0 microns (See FIG. 10).

C. In a manner similar to that described in Example 6, treat hydroxyleverninomicin B with sodium hydroxide to obtain hydroxylaminoeverninomicin B sodium salt.

EXAMPLE 11

Nitrosoeverninomicins B and C

In a manner similar to that set forth in Example 2A treat each of hydroxylaminoeverninomicin B (prepared and purified as described in Example 9) and hydroxylaminoeverninomicin C (prepared and purified as described in Example 9) in a tetrahydrofurane solution and treat with aqueous sodium hypobromite at room temperature. Isolate and purify each of the resultant products to obtain nitrosoeverninomicin B and nitrosoeverninomicin C, respectively.

EXAMPLE 12

Nitrone Derivatives of Hydroxylaminoeverninomicins B and C

In a manner similar to that described in Examples 3 to 5 treat each of hydroxylaminoeverninomicin B and hydroxylaminoeverninomicin C in anhydrous ethanol with benzaldehyde, 2-furfuraldehyde and heptaldehyde, respectively.

Isolate and purify each of the resultant products in a manner similar to that described in Examples 3–5 to obtain the benzyl nitrone, furfuryl nitrone and the heptyl nitrone derivatives, respectively, of hydroxylaminoeverninomicin B and hydroxylaminoeverninomicin C, respectively.

The present invention includes within its scope pharmaceutical compositions comprising our novel reduction products of everninomicins B, C, and D in association with a compatible, pharmaceutically acceptable carrier or coating. Also included within our invention is the method of eliciting an antibacterial response in a warm-blooded animal having a susceptible bacterial infection which comprises administering to said animal a non-toxic, antibacterially effective amount of a member selected from the group consisting of nitrosoeverninomicin B, nitrosoeverninomicin C, nitrosoeverninomicin D, hydroxylaminoeverninomicin B, hydroxylaminoeverninomicin C, hydroxylaminoeverninomicin D, nitrone derivatives of said hydroxyaminoeverninomicins, and pharmaceutically acceptable salts of the foregoing.

The compositions may be administered parenterally, orally, or topically, parenteral administration being preferred. In carrying out the methods of this invention, the active ingredient is normally combined with conventional pharmaceutical diluents and carriers which are based up the desired route of administration.

The parenteral route is preferred, particularly with alts of hydroxylaminoeverninomicin D, due to the increased absorption and rapid excretion when administered parenterally of our everninomicin reduction products as compared with their everninomicin B, C, and D precursors. In carrying out the method, the active group can, if desired, be combined with other therapeutically active compositions customarily included in anti-bacterial formulations.

The individual unit dosage and frequency of administration is determined not only by the nature and severity of the bacterial infection for which relief is sought, but also upon age, weight, species, underlying physical condition and route of administration. The exact amount to be administered should be nontoxic, yet pharmaceutically effective in alleviating the symptoms of bacterial infections. Generally, for the treatment of bacterial infections, the compositions are administered parenterally so as to give a daily dose of from 1 to about 15 mgm/kg of a reduced everninomicin compound of this invention.

The following example illustrates a pharmaceutical composition according to the invention.

EXAMPLE 13

| Parenteral Solution | Mg. |
|---|---|
| Hydroxylaminoeverninomicin D sodium salt | 58.14 |
| Sodium chloride | 5.0 |
| Sodium bisulfite | 1.625 |
| Sodium hydroxide (1N to pH 8.7) | 0.56 |
| Purified Water, q.s. 1 ml. | |

PROCEDURE

Sparge with nitrogen about 90% of the required amount of water. With stirring, add the sodium chloride and sodium bisulfite and stir until dissolved. Add the hydroxylaminoeverninomicin D sodium salt and with stirring add 1N sodium hydroxide until the solution reaches a pH of 8.7. Add water to make a total volume of 1 ml. filter through a sterilizing membrane. With this solution, fill multiple dose vials. Lyophilize.

EXAMPLE 14

| Parenteral Solution | Mg. |
|---|---|
| Hydroxylaminoeverninomicin D sodium salt | 58.14 |
| Sodium chloride | 5.0 |
| Sodium bisulfite | 1.625 |
| Sodium hydroxide (1N to pH 8.7) | 0.56 |
| Methylparaben | 1.8 |
| Propylparaben | 0.2 |
| Purified Water, q.s. 1 ml. | |

PROCEDURE

Sparge with nitrogen about 90% of the required amount of water and heat the water to a temperature of about 60°–70° C. Add the methylparaben and propylparaben, stir until dissolved, then cool the solution to 25°–30° C. Then follow the procedure described in Example 13.

EXAMPLE 15

| Parenteral Suspension | |
|---|---|
| Parental Suspension: | Mg. |
| Hydroxylaminoeverninomicin D | 100 |
| Sodium carboxymethylcellulose | 3 |
| Polysorbate 80 USP | 1 |
| Methylparaben | 3.6 |
| Propylparaben | 0.4 |
| Water, q.s. 2.0 ml. | |

PROCEDURE

1. Prepare a solution of sodium carboxylmethylcellulose, Polysorbate 80, U.S.P., methylparaben, and propylparaben.
2. Aseptically, slurry hydroxylaminoeverninomicin D with a portion of the above vehicle and pass through a colloid mill.
3. Mix the milled slurry with the remainder of the vehicle.
4. Fill into the sterile vials.

We claim:

1. The method of eliciting an antibacterial response in a warm-blooded animal having a susceptible bacterial infection, which comprises administering to said animal a non-toxic, antibacterially effective amount of a member selected from the group consisting of nitrosoeverninomicin B, nitrosoeverninomicin C, nitrosoeverninomicin D, hydroxylaminoeverninomicin B, hydroxylaminoeverninomicin C, hydroxylaminoeverninomicin D, nitrone derivatives of said hydroxylaminoeverninomicins B, C and D, and pharmaceutically acceptable salts thereof.

2. The method of claim 1 when carried out with a member selected from the group consisting of hydroxylaminoeverninomicin D, nitrone derivatives of hydroxylaminoeverninomicin D, and pharmaceutically acceptable salts thereof.

3. The method of claim 2 when carried out with a sodium salt of hydroxylaminoeverninomicin D.

4. The method of claim 2 when carried out with the N- methyl glucamine salt of hydroxylaminoeverninomicin D.

5. The method of claim 3 when administered parenterally.

6. The method of claim 4 when administered parenterally.

* * * * *

UNITED STATES PATENT OFFICE
CERTIFICATE OF CORRECTION

Patent No. 4,006,225      Dated February 1, 1977

Inventor(s) Ashit K. Ganguly et al

It is certified that error appears in the above-identified patent and that said Letters Patent are hereby corrected as shown below:

Column 6, line 68, "is dilute" should read ---in dilute---.
Column 11, lines 50-60, Table 1, Second and Third Columns,
"Hydroxylaminoeverninomicin D     Sodium salt and N-methylgluca-
                                                  mine salt minoeverninomicin D 0.3-0.8                      0.08-0.8
      0.5-5                        0.2-1.0
        30                             25

500
                                     500
                                   >2000

20-30
                                   30-40"

should read

---Hydroxylaminoeverninomicin D     Sodium salt and N-methylglu-
                                                    camine salt of hydroxylamino-
                                                    everninomicin D 0.3-0.8                         0.08-0.8
                                    0.2-1.0
                                    25
                                    0.5-5
                                    500
                                    500
                                    >2000
                                      30
                                    20-30
                                    30-40---.

UNITED STATES PATENT OFFICE
CERTIFICATE OF CORRECTION

Patent No. 4,006,225      Dated February 1, 1977

Inventor(s) Ashit K. Ganguly et al

It is certified that error appears in the above-identified patent and that said Letters Patent are hereby corrected as shown below:

Column 15, line 27, "by '$\varepsilon$' is meant '$\varepsilon\%_{cm}$'" should read ---by "$\varepsilon_1^1$" is meant "$\varepsilon_{1cm}^{1\%}$"---. Column 17, line 39, "Bioassay: Absorption" should read ---Infrared Absorption---. Column 20, line 28, "with 34%" should read ---with 35%---. Column 21, line 22, " methanol 290 mµ," should read --- $\lambda_{max}$ methanol 290 mµ,---. Column 23, line 1, "with alts" should read ---with salts---.

Signed and Sealed this

Third Day of May 1977

[SEAL]

Attest:

RUTH C. MASON
*Attesting Officer*

C. MARSHALL DANN
*Commissioner of Patents and Trademarks*